United States Patent [19]

Soedjak et al.

[11] Patent Number: 5,417,990
[45] Date of Patent: May 23, 1995

[54] READY-TO-EAT, MULTI-COMPONENT, MULTI-COLORED GELS

[75] Inventors: Helena S. Soedjak, North Tarrytown; Joseph E. Spradlin, Monroe, both of N.Y.

[73] Assignee: Kraft Foods, Inc., Northfield, Ill.

[21] Appl. No.: 219,606

[22] Filed: Mar. 29, 1994

[51] Int. Cl.$^6$ ............................................. A23L 1/0562
[52] U.S. Cl. ........................................ 426/89; 426/103; 426/262; 426/249; 426/540; 426/573; 426/575; 426/576
[58] Field of Search ................ 426/89, 103, 262, 249, 426/540, 573-579

[56] References Cited

U.S. PATENT DOCUMENTS 4,906,489  3/1990  Flango ............................... 426/579

OTHER PUBLICATIONS

Richelle et al., "The Binding of 1-Anilino-8-naphthalene Sulfonate to the Hemocyanin of *Octopus vulgaris*", Eur. J. Biochem., vol. 94 (1979), pp. 199-205.

Samanta et al., "Interaction of 8-Anilino-1-naphthalene Sulphonic Acid with UDPglucose 4-Ephimerase from *Saccharomyces fragilis*", Indian Journal of Biochemistry & Biophysics, vol. 19 (Oct. 1982), pp. 320-323.

Chou et al., "Tryptophan and 8-Anilino-1-naphthalenesulfonate Compete for Binding to Trp Repressor", The Journal of Biological Chemistry, vol. 264, No. 31 (Nov. 5, 1989), pp. 18309-18313.

*Primary Examiner*—Joseph Golian
*Attorney, Agent, or Firm*—Thomas R. Savoie; Thomas A. Marcoux

[57] ABSTRACT

Multi-component (e.g., multi-layered) and multi-colored gelled products, such as gelatin dessert gels, are prepared using water-soluble colorants and complexing agents for the colorants which will prevent the colorant from migrating within the gelled layer. The complexing agents are polyamino acids and protein materials which fluoresce with ANS.

16 Claims, No Drawings

5,417,990

READY-TO-EAT, MULTI-COMPONENT, MULTI-COLORED GELS

Consumers have in recent times been desirous of eating wholesome and fat-free snack foods and desserts. Gelled foodstuffs, such as gelatin gels fill this need. Consumers are, however, requiring that the foods they eat, particularly snack foods and dessert items, be essentially ready-to-eat.

To fill the desire of consumers for dessert or snack items which require no preparation on the part of the consumers, there exists ready-to-eat dessert gels which are usually marketed in single-service portions. These gels may be either refrigerated or shelf-stable and contain gelatin, carrageenan or other food-approved gelling agents either alone or in combination.

It has also been known to produce layered, dessert gels with adjacent layers having distinctly differing colors. Typically these layered gels are produced by first forming a bottom gelled layer and then adding an upper layer onto the already gelled bottom layer. When this is done in the home environment, the layered dessert is normally fully-consumed within a few days so that the bleeding or migration of color between adjacent layers is not a problem. For ready-to-eat gelled desserts, which must be stable through a distribution, sale and use cycle which might last several months color migration has heretofore prevented the marketing of multi-layered, multi-colored gelled desserts.

SUMMARY OF THE INVENTION

This invention relates to the formation of multi-component (e.g., multi-layered), multi-colored gelled foodstuffs wherein adjacent layers differ in color, with the gelled foodstuff being stable to color migration between components over an extended period of time. According to this invention each gelled component which contains a water-soluble colorant also contains an agent which complexes with the colorant to produce a water-soluble complex which, due to its size, does not migrate within the gel matrix and does not migrate into adjacent components. Migration of a colorant within a gel is dependent upon the pore size of the gel which in turn is inversely proportional to the concentration of the gelling agent.

The complexing agents suitable for use in this invention include polyamino acids, such as polyarginine, polylysine and polyhistidine, and protein materials which complex with 8-anilino-1-naphthalene-sulfonic acid (ANS), such as serum albumin, egg protein, alcohol dehydrogenase and soluble fractions of wheat gluten and caseinate.

DESCRIPTION OF THE INVENTION

Multi-component, gelled, ready-to-eat foodstuffs can be produced by introducing a first, gellable liquid into a container, allowing the liquid to gel to an extent which will support an adjacent upper layer, and then introducing a second gellable liquid into the container. Alternatively it would be possible to insert preformed portions (e.g., fruit pieces or fruit gels) into a container which contains a gellable liquid to achieve a multi-component product. In the case of single-serving dessert gels the container is usually a clear, plastic-cup made from a resin, such as polyethylene terephalate or polypropylene.

Multi-layered dessert gels which have a plurality of colors and flavors constitute a novel and appealing snack item. Two or more layers could be utilized with each layer having its own color, including the possibility of a clear layer, and a compatible flavor, such as cherry flavor for red, lime flavor for green, lemon flavor for yellow, etc. Such products, however, must maintain a clear line of demarcation between different colored layers in order to preserve their attractive and appealing appearance. Obviously this would require that the colorants used in any one gelled layer not migrate into an adjacent layer.

This invention would also be useful in gels which contain fruit or fruit gel inlays in which migration of colorant from the gel into the inlay is undesirable. The invention is applicable across a wide variety of gelled foodstuffs, including dessert gels, jellies, candies, pie fillings, etc.

The crux of the instant invention is the identification of a variety of water-soluble compounds which are capable of forming water-soluble complexes with commonly-used food colorants, such as those designated in the United States as FD&C dyes. The complexes formed in accordance with this invention are believed to be held together by association of hydrophobic regions within the colorant and the complexing agent, by charge-charge interaction between attracting charges on the colorant and the complexing agent, or by a combination of these forces. In order to be commercially practical the complexes must remain stable over time and not precipitate or adversely effect the hue or intensity of the colorant. Naturally, this stability must be maintained under the conditions of use which, in the case of fruit-flavored gels, will include a pH of about 3.2 to 4.5, at either ambient or refrigerated conditions, over a period of several months.

The composition of the gel is not critical and any of the food-approved gelling agents which have the functionality required for the desired end product may be employed. Among the most common gelling agents for dessert gels are gelatin, carrageenan, alginates, pectin and starch either alone or in combination. The gels may also contain any of the food ingredients normally employed in the respective products such as sweetening agents (e.g., sugars, aspartame and saccharin), acids, buffers, flavors, fruit juice and solid inlays, such as fruit pieces, vegetable pieces and nuts.

The colorant complexation which is believed necessary to prevent migration has been found to most readily occur at a pH of 4.0 or below. The level of complexation appears to decrease at pH's of 4.5 and above.

The colorant complexing agents suitable for use in this invention include soluble protein materials which under a standardized ANS test, as defined below, show a relative fluorescence intensity of at least 100, preferably at least 200 and most preferably at least 300.

Among the effective protein materials are alcohol dehydrogenase, serum albumin, egg protein, water-soluble fraction of wheat gluten, and water-soluble fraction of casein.

The soluble wheat gluten fraction employed in this invention is obtained by preparing an aqueous mixture containing 5 mg/mL of wheat gluten, 0.2 mg/mL of adipic acid and 5 mg/mL of L-cysteine. This mixture is incubated for three hours at 60° C. with continuous stirring and centrifuged to separate the insoluble fraction. Under these conditions about 87% by weight of the wheat gluten is solubilized.

A soluble caseinate fraction is prepared for ANS testing by adding sodium caseinate at 1 mg/mL to a dilute citrate solution having a pH of 4.0 and holding for 30 minutes at room temperature. The aqueous mixture is then centrifuged to separate the insoluble fraction. Under these conditions about 25% by weight of the caseinate is solubilized.

ANS in aqueous solution does not fluoresce; however, ANS undergoes a large increase in fluorescence intensity upon binding to proteins in aqueous solution due to an increase in the hydrophobicity of the microenvironment surrounding the molecule. The ANS test used to quantify the level of fluorescence for purposes of this invention utilizes common, art-recognized procedures. An ANS stock solution of 1 mM ANS is prepared in a 5 mM aqueous citrate solution having a pH of 4.0. The complexing agent stock solution is prepared at 1 mg/mL complexing agent in a 5 mM aqueous citrate solution having a pH of 4.0. The intensity of fluorescence is measured with 0.3 mL of ANS stock solution plus 2.7 mL of complexing agent stock solution using a Spectrofluorometer System 3 (Optical Devices, Inc., Elmsford, N.Y.) with an excitation wavelength of 410 nm, an emission wavelength of 446 nm, room temperature, an intensity range of 0.01, slits 5, 5, 5, 5 and a time constant of 0.3 second. The instrument was standardized to a reading of 1000 using a mixture of 0.3 mL of 1 mM ANS and 2.7 mL of absolute ethanol. The results for various protein materials which were sampled were as follows:

TABLE I

| Material | Relative Fluorescence Intensity[1] | Effective |
| --- | --- | --- |
| Yeast alcohol dehydrogenase | 1353 | Yes |
| Bovine serum albumin | 912 | Yes |
| Egg protein | 451 | Yes |
| Soluble fraction wheat gluten | 1245 | Yes |
| Soluble fraction sodium caseinate | 581 | Yes |
| Gelatin | 17 | No |
| Alginate | 2 | No |
| Agar | 2 | No |
| Clear oat protein | 5 | No |
| Hydrolyzed zein | 2 | No |
| Dextran | 13 | No |
| Soluble fraction soy protein | 6 | No |
| Soluble fraction brewer yeast | 5 | No |
| Soluble fraction lactalbumin | 5 | No |
| Soluble fraction whey protein | 69 | No |

[1]Standardized to 1000 with a 0.3 mL of 1 mM of ANS and 2.7 mL of absolute ehtanol The soluble fractions of soy protein, brewer yeast, lactalbumin and whey protein utilized in the above ANS test were obtained by preparing a mixture of the material at 1 mg/mL in aqueous 5 mM citrate at pH 4.0 at room temperature. The mixture was then centrifuged to remove any insoluble fraction and the soluble fraction was used in the ANS test.

The effectiveness or lack of effectiveness in preventing color migration is confirmed for each of the protein materials listed in Table I in a multi-layered, multi-colored gelatin product. In the case of caseinate the soluble fraction (25% by weight) was obtained by centrifuging out the insoluble fraction at a pH of 3.5 rather than 4.0 so that caseinate precipitate would not form in the gel. A first blue-colored gel was prepared by dissolving blue JELL-O ® gelatin dessert mix, containing FD&C Blue No. 1, at 0.25 g JELL-O ® powder per mL of hot water and adding the complexing agent at a level of 2 mg/mL and letting the solution cool to gel. A red-colored gelatin gel layer was then formed on top of the blue layer using red JELL-O ® containing FD&C Red No. 40 and the same preparation steps as for the blue layer. The pH of both gelatin solutions is 3.9. The multicolored, two-layered gel was stored for two months (only one month for caseinate) at refrigerated conditions and then visually evaluated for color migration. Effective materials prevented any color migration from occurring. Ineffective materials resulted first in a purple interface between the two layers, and then progressing to a homogeneous purple product after several days.

In addition to the effective protein materials noted above, it has been found that high charge density polyamino acids also function as complexing agents for water-soluble colorants.

Positively charged polyamino acids, such as polyarginine, polylysine and polyhistidine have been found useful to prevent migration of hydrophobic, negatively-charged FD&C Red. No. 40. Migration of FD&C Blue No. 1, another hydrophobic, negatively-charged colorant was prevented by polyarginine but, possible due to steric hindrance, not by polylysine or polyhistidine. The level of polyamino acid required to prevent colorant migration is inversely proportional to the molecular weight of the polyamino acid. The tested polyarginine, polylysine and polyhistidine had molecular weights in excess of 30,000. Negatively-charged polyamino acids would be useful to prevent color migration of positively-charged, water-soluble colorants.

Utilizing the above-noted multi-colored, two-layered gel storage test, this time with one layer containing an FD&C dye and the other layer being clear, migration of FD&C Red. No. 40 was prevented with each of polyarginine, polylysine and polyhistidine at level of 0.05 mg/mL. Polyarginine was also effective in preventing migration of FD&C Blue No. 1.

Typical weight levels for colorants in food gels are on the order of 1 to 200 parts per million (ppm), more typically about 4 to 150 ppm. Use levels for the soluble protein materials used in this invention will typically be from 1 to 200 times the weight level of the colorant, more typically from 5 to 150 times the weight level of colorant. Use levels for the polyamino acids will typically be from 0.05 to 10 times the weight of the colorant, more typically from 0.1 to 5 times the weight level of the colorant.

Having thus described the invention what is claimed is:

1. A multi-component gelled product wherein adjacent components are of differing colors and wherein at least one of said components contains a water-soluble colorant and either a protein material that produces a relative fluorescence intensity with a standarized ANS test of at least 100 or a polyamino acid, said protein material or polyamino acid being present in the colorant-containing gel component at a level effective to form a stable, water-soluble complex with the colorant, said complex being resistant to migration within the gel layer.

2. The multi-component gelled product of claim 1 wherein the colorant is complexed with a protein material.

3. The product of claim 2 wherein the protein material is selected from the group consisting of alcohol dehydrogenase, serum albumin, egg protein, water-soluble fractions of wheat gluten and water-soluble fractions of caseinate.

4. The multi-component gelled product of claim 1 wherein the colorant is complexed with a polyamino acid.

5. The product of claim 4 wherein the polyamino acid is selected from the group consisting of polyarginine, polylysine and polyhistidine.

6. The product of claim 1 wherein the colorant is FD&C Red. No. 40.

7. The product of claim 1 wherein the colorant is FD&C Blue No. 1.

8. The product of claim 1 wherein the gelled product is a multi-layered, dessert gel.

9. A method for preventing migration of colorants within a multi-component gelled product by adding to the formulation of each component which contains a water-soluble colorant either a protein material that produces a relative fluorescence intensity with a standardized ANS test of at least 100 or a polyamino acid, said protein material or polyamino acid being added to each colorant-containing gel component at a level effective to form a stable, water-soluble complex with the colorant, said complex being resistant to migration within the gel layer.

10. The method of claim 9 wherein a colorant is complexed with a protein material.

11. The method of claim 10 wherein the protein material is selected from the group consisting of alcohol dehydrogenase, serum albumin, egg protein, water-soluble fractions of wheat gluten and water-soluble fractions of caseinate.

12. The method of claim 9 wherein a colorant is complexed with a polyamino acid.

13. The method of claim 12 wherein the polyamino acid is selected from the group consisting of polyarginine, polylysine and polyhistidine.

14. The method of claim 9 wherein a colorant is FD&C Red No. 40.

15. The method of claim 9 wherein a colorant is FD&C Blue No. 1.

16. The method of claim 9 wherein the gelled product is a multi-layered, dessert gel.

* * * * *